(12) United States Patent
Ward

(10) Patent No.: US 11,071,580 B2
(45) Date of Patent: Jul. 27, 2021

(54) ELECTROSURGICAL ELECTRODES

(71) Applicant: COVIDIEN LP, Mansfield, MA (US)

(72) Inventor: Arlen K. Ward, Centennial, CO (US)

(73) Assignee: Covidien LP, Mansfield, MA (US)

(*) Notice: Subject to any disclaimer, the term of this patent is extended or adjusted under 35 U.S.C. 154(b) by 314 days.

(21) Appl. No.: 16/142,374

(22) Filed: Sep. 26, 2018

(65) Prior Publication Data
US 2019/0021786 A1 Jan. 24, 2019

Related U.S. Application Data

(62) Division of application No. 14/136,017, filed on Dec. 20, 2013, now abandoned.
(Continued)

(51) Int. Cl.
A61B 18/14 (2006.01)
A61B 18/00 (2006.01)
(Continued)

(52) U.S. Cl.
CPC ........ *A61B 18/1442* (2013.01); *A61B 18/149* (2013.01); *A61B 18/1485* (2013.01);
(Continued)

(58) Field of Classification Search
CPC .............. A61B 18/1485; A61B 18/149; A61B 2018/00601; A61B 2018/00976;
(Continued)

(56) References Cited

U.S. PATENT DOCUMENTS 5,658,280 A 8/1997 Issa
5,843,019 A 12/1998 Eggers et al.
(Continued)

FOREIGN PATENT DOCUMENTS

DE 10028850 C1 10/2001
JP 10014922 1/1998

OTHER PUBLICATIONS

Reich, O., et al., "Ex-vivo comparison of the haemostatic properties of standard transurethral resection and transurethral vaporization resection of the prostate", BJU International, vol. 92, pp. 319-322 (2003).
(Continued)

*Primary Examiner* — Thomas A Giuliani
(74) *Attorney, Agent, or Firm* — Carter, DeLuca & Farrell LLP

(57) ABSTRACT

An electrode assembly is provided. The electrode assembly includes a proximal end that is adapted to connect to an electrosurgical instrument including a housing defining a longitudinal axis therethrough and an electrosurgical energy source. A distal end includes a cutting electrode having a loop configuration configured to cut tissue. The distal end includes a return electrode operably disposed adjacent the cutting electrode. A dielectric shield is operably disposed between the cutting electrode and return electrode. The dielectric shield extending distally past the cutting electrode to hinder current flow to the return electrode when the dielectric shield, cutting electrode and return electrode are submersed in a conductive solution and the cutting electrode is energized, thereby concentrating current density at the cutting electrode.

8 Claims, 6 Drawing Sheets

Related U.S. Application Data

(60) Provisional application No. 61/766,483, filed on Feb. 19, 2013.

(51) Int. Cl.
    *A61B 18/12* (2006.01)
    *A61B 18/16* (2006.01)
    *A61B 17/00* (2006.01)

(52) U.S. Cl.
    CPC .............. *A61B 2017/00274* (2013.01); *A61B 2018/00083* (2013.01); *A61B 2018/00196* (2013.01); *A61B 2018/00505* (2013.01); *A61B 2018/00547* (2013.01); *A61B 2018/00601* (2013.01); *A61B 2018/126* (2013.01); *A61B 2018/1213* (2013.01); *A61B 2018/1407* (2013.01); *A61B 2018/162* (2013.01)

(58) Field of Classification Search
    CPC ...... A61B 2018/122; A61B 2018/1407; A61B 2018/141; A61B 2018/144; A61B 2018/1467; A61B 2018/1472; A61B 2018/162; A61B 2018/1213; A61B 2018/126; A61B 2018/00083
    USPC .............. 606/39, 41, 45, 46, 48; 607/98, 99, 607/104–106, 115, 116
    See application file for complete search history.

(56) References Cited

U.S. PATENT DOCUMENTS

| | | | |
|---|---|---|---|
| 6,013,076 | A | 1/2000 | Goble et al. |
| 6,050,995 | A | 4/2000 | Durgin |
| 6,142,992 | A | 11/2000 | Cheng et al. |
| 6,235,020 | B1 | 5/2001 | Cheng et al. |
| 6,296,636 | B1 | 10/2001 | Cheng et al. |
| 6,482,201 | B1 | 11/2002 | Olsen et al. |
| 6,632,193 | B1 | 10/2003 | Davison et al. |
| 6,837,888 | B2 | 1/2005 | Ciarrocca et al. |
| 6,974,453 | B2 | 12/2005 | Woloszko et al. |
| 7,128,742 | B2 | 10/2006 | Ohyama et al. |
| 2001/0020167 | A1 | 9/2001 | Woloszko et al. |
| 2001/0025177 | A1* | 9/2001 | Woloszko .......... A61B 18/1492 606/41 |
| 2001/0053908 | A1* | 12/2001 | Brommersma ...... A61B 18/149 606/45 |
| 2003/0130653 | A1 | 7/2003 | Sixto et al. |
| 2007/0093812 | A1* | 4/2007 | Hayashida ........... A61B 18/149 606/46 |
| 2008/0077129 | A1* | 3/2008 | Van Wyk ............. A61B 18/149 606/46 |
| 2011/0319880 | A1 | 12/2011 | Prakash et al. |

OTHER PUBLICATIONS

Wendt-Nordahl, Gunnar et al., "The Vista System: A New Bipolar Resection Device for Endourological Procedures: Comparison with Conventional Resectoscope", European Urology, vol. 46, pp. 586-590 (2004).

Extended European Search Report from Application No. 14154456.9 dated Jun. 11, 2014.

Examination Report issued in corresponding application No. 14 154 456.9 dated Aug. 11, 2015.

European Office Action issued in corresponding application No. 14 154 456.9 dated Mar. 29, 2016.

* cited by examiner

ELECTROSURGICAL ELECTRODES

CROSS-REFERENCE TO RELATED APPLICATIONS

The present application is a divisional of U.S. patent application Ser. No. 14/136,017 filed on Dec. 20, 2013, which claims the benefit of and priority to U.S. Provisional Application No. 61/766,483 filed on Feb. 19, 2013. The entire contents of each of the foregoing applications are hereby incorporated by reference herein.

BACKGROUND

Technical Field

The present disclosure relates to electrosurgical electrodes and, more particularly, to electrosurgical electrodes that provide concentrated amounts of electrosurgical energy to tissue during an electrosurgical procedure.

Background of Related Art

Currently, there are several surgical therapies utilized for treating benign prostate hyperplasia (BPH). At present, transurethral resection of the prostate (TURP) is predominant in the surgical therapy of BPH. Various alternative treatment devices, e.g., electrovaporization, needle ablation, laser, ultrasound, or microwave therapy have recently become available for treating BPH. However, for efficacy, TURP is still regarded as the reference standard by most clinicians, e.g., urologists.

In some instances, monopolar electrocautery systems in which current passes through a patient's body from an active electrode associated with a resectoscope and back to a return electrode that is typically placed on a patient's leg is utilized during TURP. Disadvantages associated with monopolar electrocautery systems when employed in the treatment of BPH include collateral damage to adjacent tissue (e.g., heating of tissue that is deeper than tissue being treated), unwanted stimulation of the nervous and/or muscle system, and/or possible malfunction of therapeutic devices in operative contact with a patient (e.g., a pacemaker). Another disadvantage associated with monopolar electrocautery systems when employed in the treatment of BPH may include the absorption of hypoosmolar irrigation fluid by a patient (commonly referred to in the art as TUR or TURP syndrome), which is typically a result of extended TURP procedures.

In view of the aforementioned disadvantages associated with monopolar electrocautery systems for treating BPH, bipolar electrocautery systems including a resectoscope with an active, e.g., cutting electrode, and one or more return electrodes placed on the same axis on the resectoscope have become increasingly popular in the treatment of BPH. More particularly, bipolar electrocautery systems typically provide high current densities to target tissue sites such that the aforementioned negative effects typically associated with the monopolar electrocautery systems are reduced and/or prevented. Moreover, bipolar electrocautery systems utilized for treating BPH typically use one or more types of physiological irrigation fluids, e.g., a solution of sodium chloride, such that the risk of TUR syndrome is reduced and/or eliminated.

While bipolar electrocautery systems utilized for treating BPH alleviate some, if not all, of the disadvantages associated with monopolar electrocautery systems for treating BPH, there still exists some practical challenges with bipolar electrocautery systems to treat BPH. More particularly, the prostate is a highly vascular organ which bleeds during a resection procedure, e.g., TURP that utilizes either monopolar or bipolar electrocautery systems. Bleeding causes a decrease in visual clarity which, in turn, may lead to a variety of intraoperative difficulties with undesirable consequences, e.g., increased convalescence. In order to minimize bleeding (i.e., increase hemostatic efficacy to the target tissue resection site) electrosurgical energy, i.e., current density, may be maximized at the target tissue resection site. However, when the active electrode is positioned in a conductive medium (e.g., a conductive fluid such as saline) a significant fraction of the applied current passes through the saline to the return electrode(s) and not to the target tissue resection site. This fraction of applied current passing through the saline to the return electrode(s) results in decreased hemostatic efficacy at the target tissue resection site. The amount of current passing through the saline to the return electrode(s) is indirectly proportional to the amount of current passing through the target tissue resection site and, thus, indirectly proportional to the hemostatic efficacy at the target tissue resection site. Moreover, this fraction of the current passing through the saline to the return electrode(s) results in TURP procedures having high power output requirements (due to the reduction of a tissue current density, which, in turn, results in overall applied power being increased to the active electrode).

In view thereof, electrosurgical electrode efficiency (i.e., improved transfer of current from the active or cutting electrode to the tissue resection site) would improve hemostatic efficacy at the tissue resection site during TURP and reduce the applied power requirements of a power source associated with the resection device and/or active electrode.

SUMMARY

An aspect of the present disclosure provides an electrode assembly. The electrode assembly includes a proximal end that is adapted to connect to an electrosurgical instrument including a housing defining a longitudinal axis therethrough and an electrosurgical energy source. A distal end includes a cutting electrode having a loop configuration configured to cut tissue. The distal end includes a return electrode operably disposed adjacent the cutting electrode. A dielectric shield is operably disposed between the cutting electrode and return electrode. The dielectric shield extending distally past the cutting electrode to hinder current flow to the return electrode when the dielectric shield, cutting electrode and return electrode are submersed in a conductive solution and the cutting electrode is energized, thereby concentrating current density at the cutting electrode.

The dielectric shield may be disposed parallel to the longitudinal axis defined by the housing and above the cutting electrode. The dielectric shield may include a generally arcuate configuration and extend laterally across the electrode assembly. Moreover, the dielectric shield may be formed from flouropolymer, polyimide, polyamide, polyaryl sulfone and silicone plastic. Further, a thickness of dielectric shield may be in the range from about 0.005 inches to 0.100 inches.

The cutting electrode may be a wire, which may be formed from a metal such as tungsten, tungsten alloys and stainless steel. A cross section of the cutting electrode may include a shape such as circular, semicircular, square, rectangular, triangular, polygonal and combinations of the above. A cross-section diameter of the wire may range from about 0.25 mm to about 4 mm. The loop configuration of the cutting electrode may include a diameter that ranges from about 3 mm to about 10 mm.

An aspect of the present disclosure provides an electrosurgical instrument. The electrosurgical instrument includes an elongated housing having a lumen defining a longitudinal axis therethrough. The electrosurgical instrument having distal and proximal ends. The proximal end adapted to connect to electrosurgical energy source. An electrode assembly includes a proximal end adapted to connect to the distal end of the elongated housing and a distal end including a cutting electrode having a loop configuration configured to cut tissue. The distal end including a return electrode operably disposed adjacent the cutting electrode. A dielectric shield is operably disposed between the cutting electrode and return electrode. The dielectric shield extending distally past the cutting electrode to hinder current flow to the return electrode when the dielectric shield, cutting electrode and return electrode are submersed in a conductive solution and the cutting electrode is energized, thereby concentrating current density at the cutting electrode.

An aspect of the present disclosure provides an electrode assembly. The electrode assembly includes a proximal end that is adapted to connect to an electrosurgical instrument including a housing defining a longitudinal axis therethrough and an electrosurgical energy source. A distal end includes a cutting electrode having a loop configuration configured to cut tissue. The distal end includes a return electrode operably disposed adjacent the cutting electrode. An insulative material is operably disposed between the cutting electrode and return electrode to hinder current flow to the return electrode when the insulative material, cutting electrode and return electrode are submersed in a conductive solution and the cutting electrode is energized, thereby concentrating current density at the cutting electrode.

The insulative material may be disposed parallel to the longitudinal axis defined by the housing and above the cutting electrode. A proximal end of the cutting electrode may include a pair of curved sections. The insulative material may be operably disposed along the pair of curved sections of the cutting electrode. The insulative material may be a flouropolymer, polyimide, polyamide, polyaryl sulfone, silicone plastic and polytetrafluoroethylene.

An aspect of the present disclosure provides an electrode assembly adapted to connect to an electrosurgical instrument. A proximal end of the electrode assembly is adapted to connect to an electrosurgical instrument including a housing defining a longitudinal axis therethrough and an electrosurgical energy source. A distal end of the electrode assembly includes a cutting electrode having a loop configuration configured to cut tissue. The loop configuration of the cutting electrode has a non-uniform cross-section diameter. The distal end includes a return electrode that is operably disposed adjacent the cutting electrode. The non-uniform cross-section diameter of the cutting electrode hinders current flow to the return electrode when the cutting electrode and return electrode are submersed in a conductive solution and the cutting electrode is energized, thereby concentrating current density at the cutting electrode.

A top portion of the loop configuration of the cutting electrode may include a thicker diameter than a bottom portion of the loop configuration of the cutting electrode such that when the cutting electrode is energized current density adjacent the bottom portion and surrounding tissue is greater than current density at the top portion.

Yet another aspect of the present disclosure provides an electrosurgical instrument. The electrosurgical instrument includes an elongated sheath including a sheath lumen, a distal end and a proximal end. An electrode assembly includes a proximal end adapted to connect to an electrosurgical instrument including a housing defining a longitudinal axis therethrough and an electrosurgical energy source. A distal end includes a cutting electrode having a loop configuration configured to cut tissue. The loop configuration of the cutting electrode has a non-uniform cross-section diameter. The distal end includes a return electrode that is operably disposed adjacent the cutting electrode. The non-uniform cross-section diameter of the cutting electrode hinders current flow to the return electrode when the cutting electrode and return electrode are submersed in a conductive solution and the cutting electrode is energized, thereby concentrating current density at the cutting electrode.

Another aspect of the present disclosure provides an electrode assembly adapted to connect to an electrosurgical instrument. A proximal end of the electrode assembly is adapted to connect to an electrosurgical instrument including a housing defining a longitudinal axis therethrough and an electrosurgical energy source. A distal end of the electrode assembly includes a cutting electrode having a loop configuration configured to cut tissue. The loop configuration of the cutting electrode having a surface finish minimizing the energy required for bubble nucleation on the cutting electrode and promoting vapor bubble adhesion. The surface finish may include a pitted finish or a hydrophobic finish. The distal end including a return electrode that is operably disposed adjacent the cutting electrode. The surface finish of the cutting electrode hinders current flow to the return electrode when the cutting electrode and return electrode are submersed in a conductive solution and the cutting electrode is energized, thereby concentrating current density at the cutting electrode.

Another aspect of the present disclosure provides an electrode assembly adapted to connect to an electrosurgical instrument. A proximal end of the electrode assembly is adapted to connect to an electrosurgical instrument including a housing defining a longitudinal axis therethrough and an electrosurgical energy source. A distal end of the electrode assembly including a cutting electrode having a loop configuration configured to cut tissue. The distal end including a return electrode that is operably disposed adjacent the cutting electrode at a distance maximizing energy per volume and minimizing heating depth such that hemostasis is maximized at a target tissue site. The distance may be in the range from about 3 mm to about 10 mm. The distal end including a return electrode operably disposed adjacent the cutting electrode. The distance between the return electrode and the cutting electrode hinders current flow to the return electrode when the cutting electrode and return electrode are submersed in a conductive solution and the cutting electrode is energized, thereby concentrating current density at the cutting electrode.

The cutting electrode and return electrode may be in fixed spaced-apart relation with respect to one another. The cutting electrode and return electrode may be in a selectably movable spaced-apart relation with respect to one another such that a variable tissue effect is achieved at the target tissue site. The return electrode may include two return electrodes operably disposed on a respective longitudinal section associated with the electrode assembly. The two return electrodes maybe slidably and axially movable with respect to each other and the cutting electrode.

BRIEF DESCRIPTION OF THE DRAWINGS

Various embodiments of the present disclosure are described hereinbelow with references to the drawings, wherein.

DETAILED DESCRIPTION

Figure 1:
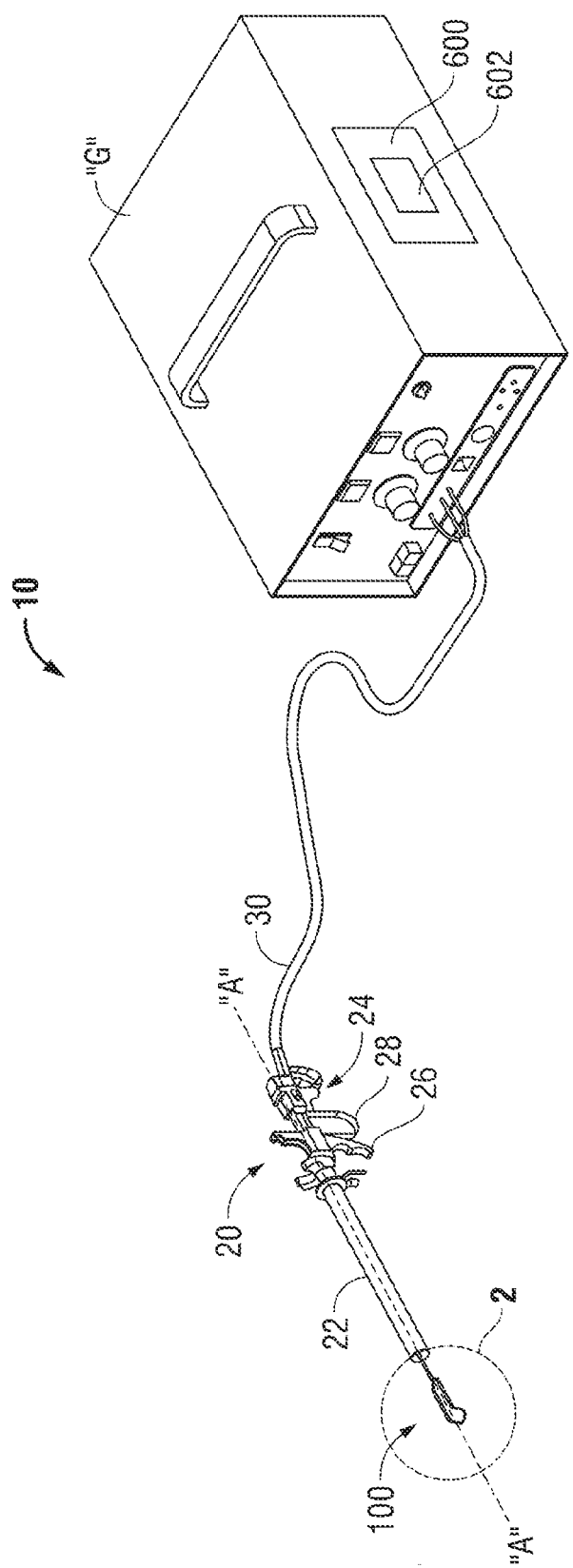
FIG. 1. is a schematic plan view of a power supply configured for use with a resectoscope intended for use with an electrode assembly in accordance with the present disclosure.

Particular embodiments of the presently disclosed electrosurgical electrode are described in detail with reference to the drawing figures wherein like reference numerals identify similar or identical elements. As used herein, the term "distal" refers to that portion of the electrosurgical electrode which is further from the user or surgeon while the term "proximal" refers to that portion of the electrosurgical electrode which is closer to the user or surgeon.

FIG. 1 sets forth a side, perspective view of an electrosurgical system 10 including an electrosurgical instrument 20 intended for use with an electrosurgical electrode assembly 100 constructed in accordance with one embodiment of the present disclosure. In the embodiment illustrated in FIG. 1, the electrosurgical instrument is a resectoscope 20. The resectoscope 20 may be any suitable type of resectoscope and may be operated in bipolar or monopolar modes. While the following description will be directed towards a resectoscope, it is envisioned that the features and concepts (or portions thereof) of the present disclosure can be applied to any electrosurgical type instrument, e.g., forceps, suction coagulators, wands, etc.

To facilitate understanding of the electrode assembly 100, a description of the resectoscope 20 illustrated in FIG. 1 now follows. Briefly, resectoscope 20 includes an elongated sheath or housing 22 with a sheath lumen extending substantially along the entire length of sheath 22. A support frame connects electrosurgical electrode assembly 100 to one or more suitable types of electrosurgical energy sources, e.g., electrosurgical generator "G." The support frame provides structural support for the electrode assembly 100 and/or one or more operative components associated with the resectoscope 20. To this end, support frame may be made of stainless or corrosion resistant material, and the like. Resectoscope 20 includes a working element 24 that is attached to sheath 22. Working element 24 of resectoscope 20 may include a stationary handle 28, a movable handle 26, an internal electrical interface, e.g., electrical socket, where a proximal end 106 of the electrode assembly 100 is plugged into and secured for electric current connection and transmission, and an external electrical interface, e.g., external socket, for plugging in an external cable 30 that transmits electric current from the energy source "G." All connections may be insulated to prevent dissipation of electric current. A portion of the electrode assembly 100, e.g., a proximal end of the electrode assembly, extends into working element 24 and operably couples to a drive mechanism operably associated with one or more components, e.g., working head 24, associated with the resectoscope 20. The drive mechanism is configured for axial translation of the electrode assembly 100 such that the electrode assembly 100 is translatable from an initial position within the sheath 22 to a subsequent position outside the sheath 22. Alternatively, the electrode assembly 100 may be fixedly coupled, i.e., non-translatable, to the distal end of the sheath 22. In one particular embodiment, a visualization apparatus fits into working element 24.

The electrode assembly 100 of the present disclosure is configured to concentrate electrosurgical energy, i.e., current density, at specific points along a cutting electrode 102 associated with the electrode assembly 100 when the electrode assembly 100 is positioned adjacent a target tissue resection site. More particularly, when electrode assembly 100 or portion thereof, e.g., a distal end including a cutting electrode 102 and return electrode 104, is positioned adjacent the target tissue resection site and within a conductive medium (e.g., saline), one or more components or configurations associated with the electrode assembly 100 improves hemostatic efficacy at the target tissue resection site by limiting the amount of current flowing back to the return electrode 104 such that a desired tissue effect is achieved at the target tissue resection site.

Figure 2:
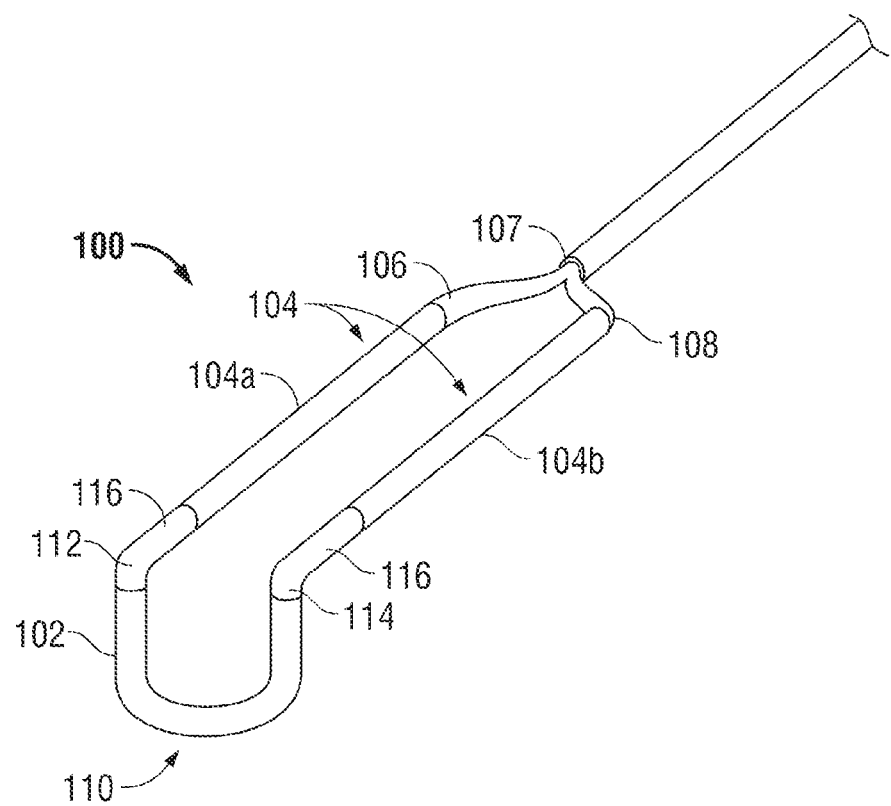
FIG. 2 is an enlarged view of the area of detail illustrated in FIG. 1.

With reference now to FIG. 2, an embodiment of the electrosurgical electrode assembly 100 is shown. Electrode assembly 100 may be fabricated from a conductive type material, such as, for example, stainless steel, tungsten, copper, etc. or may be coated with an electrically conductive material. In the embodiment illustrated in FIG. 2, electrode assembly 100 is fabricated from stainless steal. Electrode assembly 100 includes a proximal end 107 that is disposed in electrical communication with the generator "G" via the internal socket and external socket configuration described above.

Electrode assembly 100 is defined by two laterally spaced-apart longitudinal sections 106 and 108 that are parallel to a longitudinal axis "A-A" defined by the sheath 22 (FIG. 1). Each longitudinal section 106 and 108 culminates at a distal tip 110 having a cutting electrode 102 with loop geometry. Each longitudinal section 106 and 108 includes a respective generally arcuate or bent section 112 and 114. Bent sections 112 and 114 are disposed at a proximal end of the cutting electrode 102 and provide a transition in the orientation of the longitudinal sections 106 and 108 such that the cutting electrode 102 is oriented in generally orthogonal relation with respect to the longitudinal sections 106 and 108, as best seen in FIG. 2. Bent sections 112 and 114 include a relatively large radius of curvature (when compared to a radius of curvature of the loop geometry associated with the cutting electrode 102) which may result in a high current density developing at the bent sections 112 and 114 when electrosurgical energy is transmitted to the cutting electrode 102 and the cutting electrode 102 and return electrode 104 are submerged in a conductive medium; the significance of which described in greater detail below. Cutting electrode 102, as is conventional in the art, is in electrical communication with an outgoing electrical path of the generator "G." Cutting electrode 102 receives electrosurgical energy from the generator "G" and is configured to generate a current at a target tissue resection site. To this end, cutting electrode 102 may have one or more suitable loop geometries. Suitable cutting electrode 102 loop geometries include but are not limited to radial, circular, elliptical, curved, rounded, bowed, arc, arch, crescent, semicircle, roller cylinder and so forth. The cutting electrode loop may also be malleable to form one or more of the aforementioned geometries. The loop size diameter of the cutting electrode 102 may range from about 3 mm to about 10 mm, or any size that will fit in a commercially available resectoscope. In the embodiment illustrated in FIGS. 1 and 2, cutting electrode 102 includes a wire loop configuration. Alternatively, cutting electrode 102 may include a band loop configuration, wing loop configuration or other suitable loop configuration. Cross-section shapes of the wire loop configuration may include circular, semicircular (or any portion of a circle), square, rectangular, triangular, or polygonal shapes such as hexagon, octagon, flat plate, and combinations of the foregoing. The cross-section diameter of the wire loop configuration of the cutting electrode 102 may range from about 0.25 mm to about 4 mm. In certain embodiments the cross-section diameter of the wire loop may vary, as described in greater detail below.

One or more return electrodes 104 are operably disposed on the electrode assembly 100 and in electrical communication with a return electrical path of the generator "G." In the embodiment illustrated in FIG. 2, a pair of return electrodes 104a and 104b is disposed in a fixed spaced-apart relation with respect to each other and cutting electrode 102. More particularly, the pair of return electrodes 104a and 104b is operably disposed on a respective longitudinal section 106 and 108. Alternatively, a return electrode 104 may be operably disposed on one of the longitudinal sections, e.g., longitudinal section 106. Each of return electrodes 104a and 104b are positioned adjacent a respective bent section 112 and 114. Return electrodes 104a and 104b may be fabricated from any suitable conductive (or partially conductive) material. More particularly, return electrodes 104a and 104b are fabricated from a material that is equally or less conductive than the material of the cutting electrode 102. In one particular embodiment, return electrodes 104a and 104b are fabricated from stainless steal. In certain embodiments, return electrodes 104a and 104b are fabricated from a material that is equally or more conductive than the material of the cutting electrode 102.

A layer of insulative coating 116 is operably disposed on a portion of the electrode assembly 100. In the embodiment illustrated in FIGS. 1 and 2, a layer of insulative coating 116 is operably disposed between the return electrodes 104a and 104b and cutting electrode 102 and, more particularly, a layer of insulative coating is disposed along the bent sections 112 and 114. Insulative coating 116 may be made from any suitable material including but not limited to Teflon®, Teflon® polymers, silicone and the like.

In use, initially, electrode assembly 100 including cutting electrode 102 and return electrodes 104 and 104b is positioned within sheath 22 of the resectoscope. Sheath 22 is inserted into a urethra of a patient. Electrode assembly 100 including cutting electrode 102 and return electrodes 104a and 104b are deployed via movable handle 26 of resectoscope 22 from within the sheath 22 (and submerged within the conductive medium, e.g., saline) to an area adjacent a target tissue resection site, e.g., prostate of a patient. Thereafter, electrosurgical energy is transmitted to the cutting electrode 102. It is noted, the radius of curvature typically associated with bent sections of conventional electrode assemblies is larger compared to a radius of curvature associated with cutting electrodes associated with the same electrode assemblies. Accordingly, in conventional electrode assemblies, the proximity of the bent sections with respect to one or more return electrodes associated with the electrode assemblies provide a return path of least resistance for current (when compared to the target tissue resection site) effectively shunting a fraction of the current to the return electrode(s). Shunting a fraction of the current through the return electrode(s) may decrease the current density at the cutting electrode, which, in turn, decreases the hemostatic efficacy provided by the electrode assembly during a resection procedure, e.g., a TURP procedure. In accordance with the present disclosure, providing an insulative coating 116 in a manner as described herein, minimizes and/or prevents high current densities from developing adjacent the bent sections 112 and 114 during transmission of electrosurgical energy to the cutting electrode 102. Accordingly, an optimum amount of current is shunted through the return electrodes 104a and 104b and current density is concentrated at the cutting electrode 102 such that hemostatic efficacy at the target tissue resection site and power transfer from the generator "G" to the cutting electrode 102 is maximized with the electrode assembly 100.

Figure 3A:
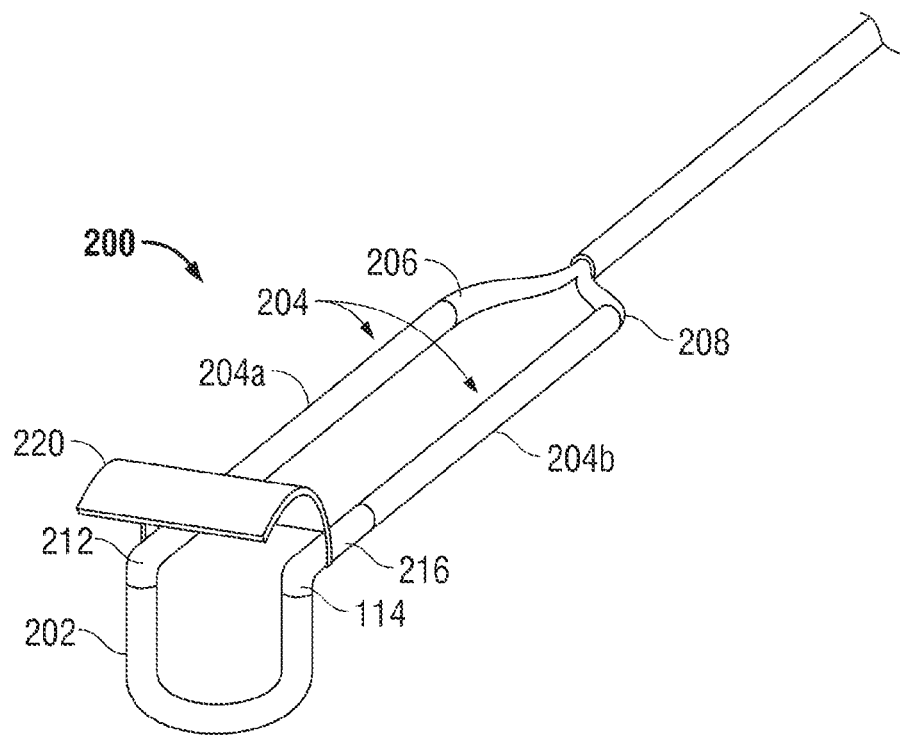
FIG. 3A is a side, perspective view of an electrode assembly in accordance with an alternate embodiment of the present disclosure.
Figure 3B:
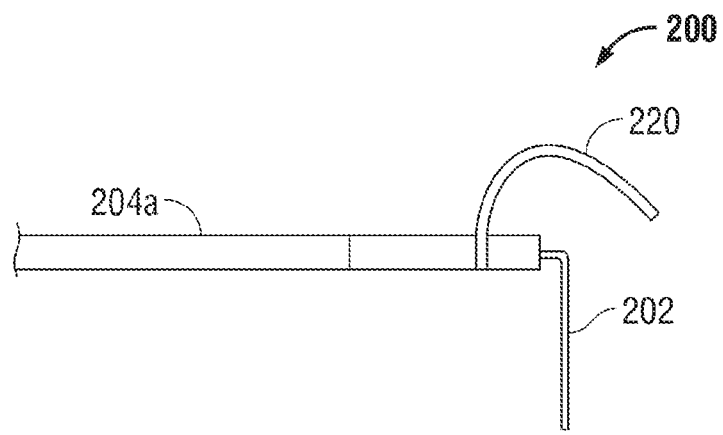
FIG. 3B is a partial, side view of the electrode assembly depicted in FIG. 3A.

With reference to FIGS. 3A and 3B, an alternate embodiment of electrode assembly 100 is shown and designated electrode assembly 200. Electrode assembly 200 is substantially similar to that of electrode assembly 100 and so as not to obscure the present disclosure with redundant information, only those features that are unique to electrode assembly 200 are described in detail herein. Electrode assembly 200 is described in terms of use with resectoscope 20. Accordingly, only those operative components associated with resectoscope 20 necessary to facilitate understanding of the electrode assembly 200 are described in detail herein.

Electrode assembly includes a dielectric shield 220. Dielectric shield 220 may be made from any suitable material including but not limited to, flouropolymer, polyimide, polyamide, polyaryl sulfone, silicone plastic and the materials described above with respect to the insulative material 116. Dielectric shield 220 may have any suitable configuration. In the embodiment illustrated in FIGS. 3A and 3B, dielectric shield 220 includes a generally arcuate or concave configuration. Dielectric shield 220 is operably coupled to electrode assembly 200. More particularly, dielectric shield 220 operably couples to each of a pair of longitudinal sections 206 and 208 at distal end of the electrode assembly 200 adjacent bent sections 212 and 214. Dielectric shield 220 extends toward and past a cutting electrode 202 such that dielectric shield 220 is positioned distally relative to the cutting electrode 202. Positioning the dielectric shield 220 distally relative to the cutting electrode 202 increases a return path for current through a conductive medium, e.g., saline, to one or more return electrodes 204, e.g., return electrodes 204a and 204b, associated with electrode assembly 200 when the electrode assembly 200 including cutting electrode 202 and return electrodes 204a and 204b are positioned within the saline. Essentially, the impedance at the return electrodes 204a and 204b is higher than at the target tissue resection site resulting in a greater concentration of current at the cutting electrode 202 and adjacent the target tissue resection site. Dielectric shield 220 may be secured to the electrode assembly 200 by any securement method(s) and/or device(s) including but not limited to soldering, brazing, welding, etc. In the embodiment illustrated in FIGS. 3A and 3B, dielectric shield 220 is welded to each of the longitudinal sections 206 and 208. Alternatively, dielectric shield 220 may be operably associated with the resectoscope 20 and positionable adjacent cutting electrode 202 during a TURP procedure. Dielectric shield 220 may have any suitable dimensions, e.g., width, height, thickness, etc. In one particular embodiment, a thickness of dielectric shield 220 ranges from about 0.005 inches to about 0.100 inches.

Operation of a resectoscope 20 with an electrode assembly 200 is substantially similar to that of electrode assembly 100. In use, electrode assembly 200 including dielectric shield 220, cutting electrode 202 and return electrodes 204a and 204b is deployed via movable handle 26 of resectoscope 22 from within the sheath 22 (and submerged within the conductive medium, e.g., saline) to an area adjacent a target tissue resection site. Dielectric shield 220 increases a return path for current through the saline to return electrodes 204a and 204b. The impedance at the return electrodes 204a and 204b is higher than at the target tissue resection site resulting in a greater concentration of current at the cutting electrode 202 and adjacent the target tissue resection site. Accordingly, an optimum amount of current is shunted through the return electrodes 204a and 204b and current density is concentrated at the cutting electrode 202 such that hemostatic efficacy at the target tissue resection site and power transfer from the generator "G" to the cutting electrode 202 is maximized with the electrode assembly 200.

Figure 4A:
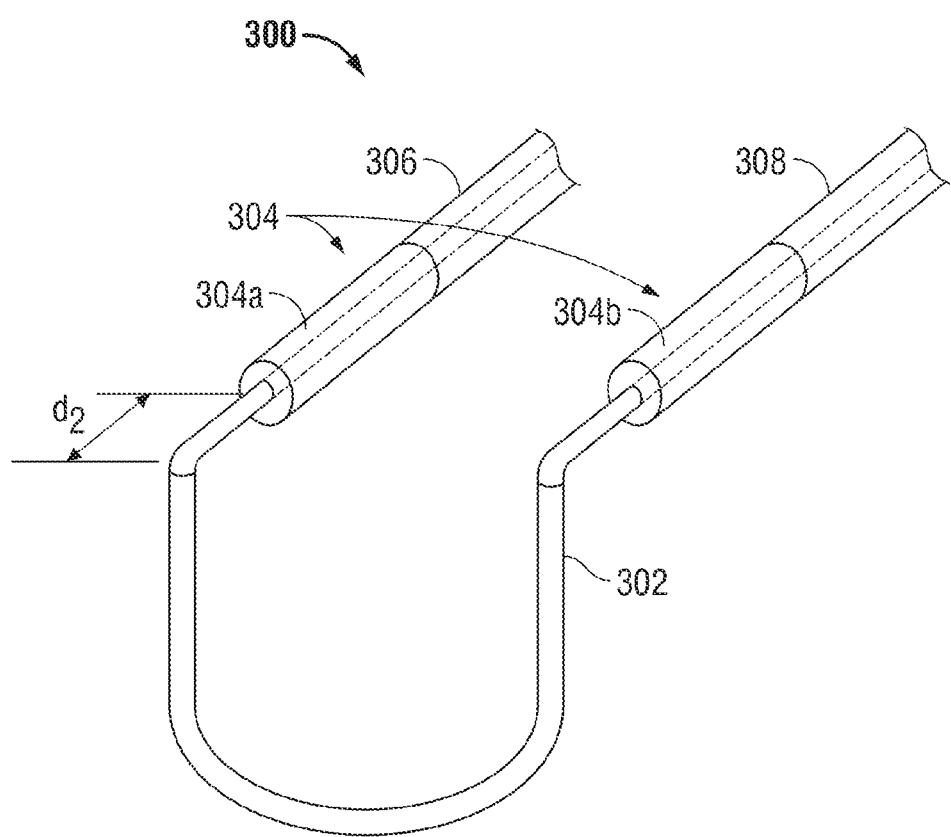
FIG. 4A is a side, perspective view of an electrode assembly in accordance with an alternate embodiment of the present disclosure.
Figure 4B:
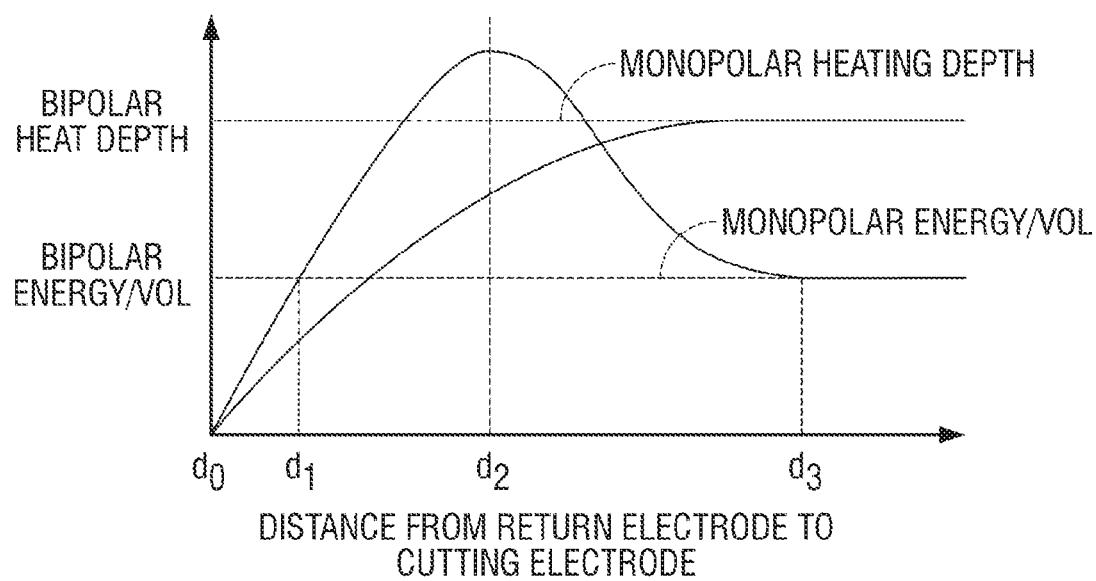
FIG. 4B is a graphical representation of a relationship between heating depth and energy per volume versus distance from a return electrode to an active electrode.

With reference to FIGS. 4A and 4B, and initially with reference to FIG. 4A, an alternate embodiment of electrode assemblies 100 and 200 is shown and designated electrode assembly 300. Electrode assembly 300 is substantially similar to that of electrode assemblies 100 and 200. So as not to obscure the present disclosure with redundant information, only those features that are unique to electrode assembly 300 are described in detail herein. Electrode assembly 300 is described in terms of use with resectoscope 20. Accordingly, only those operative components associated with resectoscope 20 necessary to facilitate understanding of the electrode assembly 300 are described in detail herein.

In accordance with the present disclosure, hemostasis is a combination of heating depth and energy per volume. Heating depth and/or energy per volume can both be modified by varying a distance "d" between a cutting electrode, e.g., a cutting electrode 302, and one or more return electrodes, e.g., a return electrode 304 including a pair of return electrodes 304a and 304b. The relationship of heating depth and energy per volume versus a distance between cutting electrode 302 and return electrodes 304a and 304b is illustrated in FIG. 4B. At a distance where "d" is equal to zero, e.g., "d0", cutting electrode 302 and return electrodes 304a and 304b are shorted together. As the distance "d" increases between the cutting electrode 302 and return electrodes 304a and 304b, the behavior of both heating depth and energy per volume will approach that of a monopolar electrocautery system (see FIG. 4B at distance "d3") that includes a cutting electrode and one or more return electrodes positioned on a patient's body. At some intermediate distance "d" (e.g., a distance "d2" where "d1"<"d2"<"d3"), the energy volume is higher in a bipolar electrocautery system when compared to a monopolar electrocautery system. In accordance with the present disclosure, this behavior is utilized to develop an electrode assembly 300 that maximizes hemostasis and energy per volume at a target tissue resection site, with minimal heating depth required at the target tissue resection site resulting in less collateral damage to adjacent tissue.

To this end, cutting electrode 302 and return electrodes 304a and 304b are in a fixed spaced-apart relationship relative to each other and separated at a distance "d2" where "d1"<"d2"<"d3." In one particular embodiment, cutting electrode 302 and return electrodes 304a and 304b are separated by a distance "d2" where "d2" ranges from about 3 mm to about 10 mm. In one particular embodiment, cutting electrode 302 and return electrodes 304a and 304b are separated by a distance "d2" that is equal to 5 mm. This distance "d2" permits sufficient time for current density at the cutting electrode 302 to build-up without interference from the return electrode 304, i.e., shunting effect of current through saline to the return electrodes 304a and 304b, such that tissue may be cut.

Figure 4C:
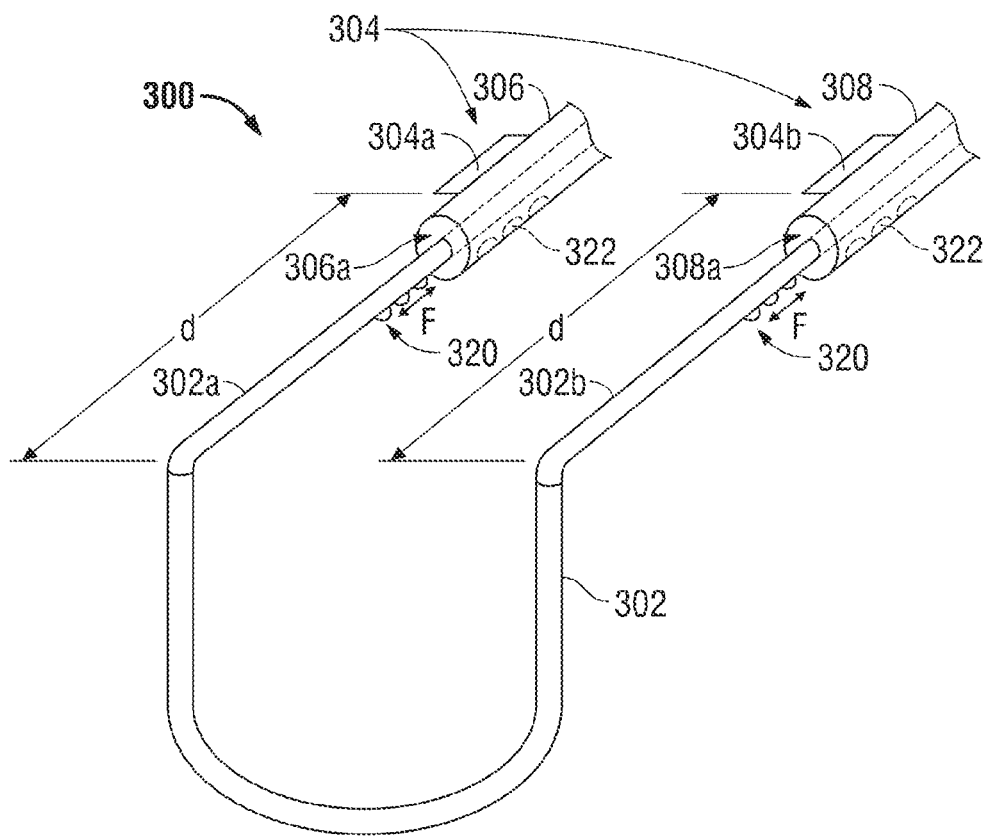
FIG. 4C is a side, perspective view of an electrode assembly in accordance with an alternate embodiment of the electrode assembly depicted in FIG. 4A.

In an embodiment (FIG. 4C), electrode assembly 300 may be designed with a user-selectable distance "d" interface. In this instance, the distance between the cutting electrode 302 and return electrodes 304a and 304b may be varied before a TURP procedure or, in some instances, during a TURP procedure such that a desired tissue effect can be achieved at a target tissue site, e.g., resection of tissue with adequate hemostasis to tissue at the target tissue site. With this purpose in mind, each of longitudinal sections 306 and 308 may include a respective substantially hollow internal portion 306a and 308a configured to slidably receive corresponding elongated portions 302a and 302b associated with the cutting electrode 302. More particularly, a mechanical interface (e.g., a friction fit mechanical interface or a indent and detent interface between the internal portions 306a and 308a and the corresponding elongated portions 302a and 302b) maintains the cutting electrode 302 in a substantially fixed, spaced-apart relation with respect to the return electrodes 304a and 304b that are operably positioned on respective elongated portions 306 and 308. More particularly, in the embodiment illustrated in FIG. 4C, one or more detents 320 (three detents shown for illustrative purposes) operably disposed along a length of each of the elongated portions 302a and 302b is configured to releasably engage one or more corresponding indents 322 (shown phantomly) operably disposed along a length of the internal sections 306a and 308a. In this instance, when a predetermined force is applied to the cutting electrode 302, the elongated portions 302a and 302b, and/or the elongated sections 306 and 308, the detent(s) 320 is forced out of engagement with the indent(s) 322 such that the cutting electrode 302 (including elongated portions 302a and 302b associated therewith) are movable relative to the longitudinal sections 306 and 308. More particularly, the cutting electrode 302 including elongated portions 302a and 302b associated therewith may be "pushed" proximally into and/or "pulled" distally away from the corresponding internal portions 306a and 308a associated with the longitudinal sections 306 and 308 (see directional arrow "F" in FIG. 4C, for example).

Operation of a resectoscope 20 with an electrode assembly 300 is substantially similar to that of electrode assemblies 100 and 200. In use, electrode assembly 300 including cutting electrode 302 and return electrodes 304a and 304b is deployed via movable handle 26 of resectoscope 22 from within the sheath 22 (and submerged within the conductive medium, e.g., saline) to an area adjacent a target tissue resection site. Cutting electrode 302 and return electrodes 304a and 304b are separated by a distance "d2" where "d2" ranges from about 3 mm to about 5 mm. As noted above, this distance "d2" permits sufficient time for current density at the cutting electrode 302 to build-up without interference from the return electrode 304 (i.e., shunting effect of current through saline to the return electrodes 304a and 304b) such that tissue may be cut. Accordingly, an optimum amount of current is shunted through the return electrodes 304a and 304b and current density is concentrated at the cutting electrode 302 such that hemostatic efficacy at the target tissue resection site and power transfer from the generator "G" to the cutting electrode 302 is maximized with the electrode assembly 300.

Figure 5:
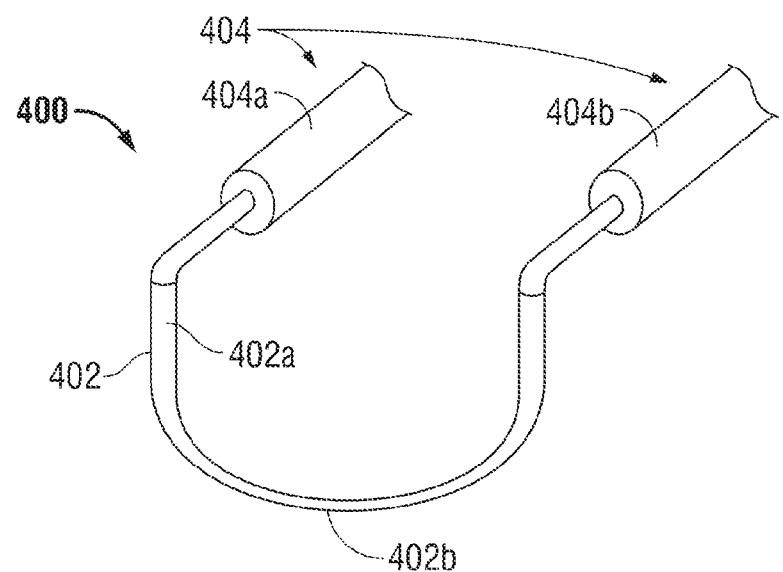
FIG. 5 is a side, perspective view of an electrode assembly in accordance with an alternate embodiment of the present disclosure.

With reference to FIG. 5, an alternate embodiment of the electrode assemblies 100, 200 and 300 is shown and designated electrode assembly 400. Electrode assembly 400 is substantially similar to that of electrode assemblies 100, 200 and 300. So as not to obscure the present disclosure with redundant information, only those features that are unique to electrode assembly 400 are described in detail herein. Electrode assembly 400 is described in terms of use with resectoscope 20. Accordingly, only those operative components associated with resectoscope 20 necessary to facilitate understanding of the electrode assembly 400 are described in detail herein.

Cutting electrode 402 includes a cross-section loop diameter that varies. More particularly, a top portion 402a of the cutting electrode 402 is thicker than a bottom portion 402b of the cutting electrode 402. In this instance, bottom portion 402b of cutting electrode 402 provides a radius of curvature that is smaller than a radius of curvature of a top portion 402a of the cutting electrode 402. Accordingly, an electric field at the bottom portion 402b, i.e., having the smaller radius of curvature, is increased resulting in an increase in current density at the bottom portion 402b and adjacent a target tissue resection site. Top portion 402a and bottom portion 402b may have any suitable diameter. In the embodiment illustrated in FIG. 5, bottom portion 402b has a diameter that ranges from about 0.0012 inches to about 0.0016 inches at its thinnest point. As illustrated in FIG. 5, the cross-section diameter of the cutting electrode 402 gradually increases from the bottom portion 402b toward the top portion 402a. This gradual increase prevents "hot spots" from developing across portions of the cutting electrode 402. Varying the cross-section diameter of the cutting electrode 402 may provide one or more additional advantages when compared to certain conventional electrode assemblies. More particularly, the thicker top portion 402a, which is less likely to "breakdown," e.g., arc, of the cutting electrode 402 may be utilized for coagulating and the thinner bottom portion 402b of the cutting electrode 102, which is more likely to arc, may be used for cutting.

Operation of a resectoscope 20 with an electrode assembly 400 is substantially similar to that of electrode assemblies 100, 200 and 300. In use, electrode assembly 400 including cutting electrode 402 and a return electrodes 404 including return electrodes 404a and 404b are deployed via movable handle 26 of resectoscope 22 from within the sheath 22 (and submerged within the conductive medium, e.g., saline) to an area adjacent a target tissue resection site. Bottom portion 402b of cutting electrode 402 provides a radius of curvature that is smaller than a radius of curvature of a top portion 402a of the cutting electrode 402. Accordingly, the electric field at the bottom portion 402b is larger resulting in an increase in current density at the bottom portion 402b and adjacent the target tissue resection site. Accordingly, an optimum amount of current is shunted through the return electrodes 404a and 404b and current density is concentrated at the cutting electrode 402 such that hemostatic efficacy at the tissue resection site and power transfer from the generator "G" to the cutting electrode 402 is maximized with the electrode assembly 400.

Figure 6:
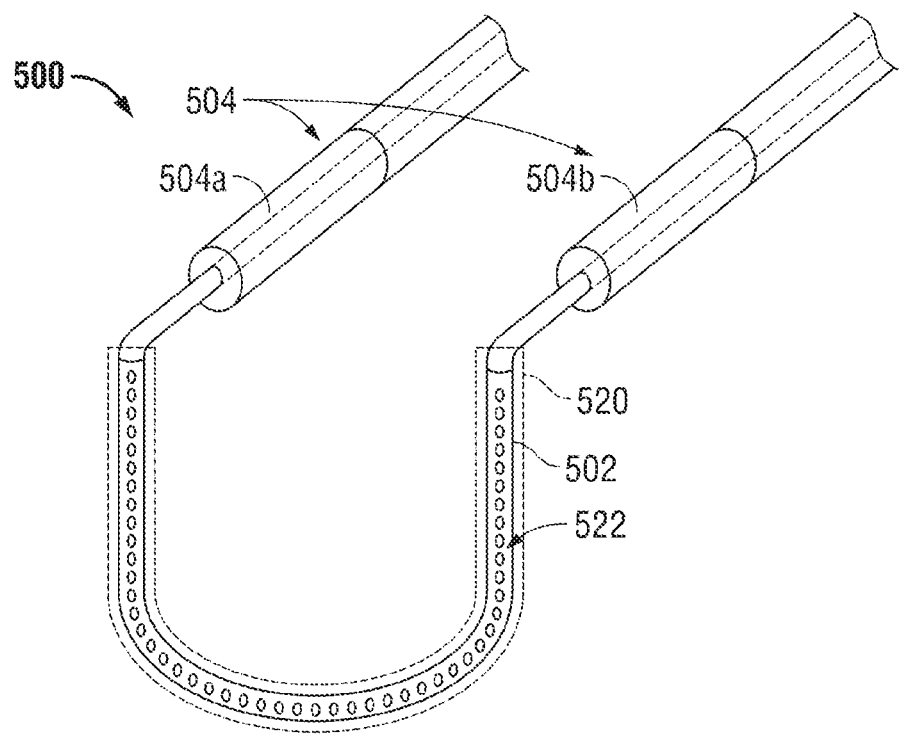
FIG. 6 is a side, perspective view of an electrode assembly in accordance with an alternate embodiment of the present disclosure.

With reference to FIG. 6, an alternate embodiment of the previously described electrode assemblies 100, 200, 300 and 400 is shown and designated electrode assembly 500. Electrode assembly 500 is substantially similar to that of electrode assemblies 100, 200, 300 and 400.

In conventional electrode assemblies, during initiation of a cutting pass of a cutting electrode, a delay is typically required for an arc discharge to develop at the cutting electrode. This delay may be attributed to a low impedance of the conductive medium, e.g., saline, surrounding the cutting electrode when the cutting electrode is initially submerged in the saline. In accordance with present disclosure, the cutting electrode 502 includes one or more types of surface finishes that promotes and/or facilitates vapor bubble adhesion or minimizes the energy required for bubble nucleation on the cutting electrode 502, which, in turn, minimizes the time delay for an arc to develop at the cutting electrode 502. To this end, cutting electrode 502 includes a surface finish that includes a hydrophobic finish 520 (shown phantomly for illustrated purposes), a textured finish (e.g., a pitted finish 522), and/or combination thereof. In the embodiment illustrated in FIG. 5 a plurality of pits 522 is operably disposed along a length of the cutting electrode 502 with a hydrophobic coating 520 substantially surrounding the cutting electrode 502 including the plurality of pits 522.

Operation of a resectoscope 20 with an electrode assembly 500 is substantially similar to that of electrode assemblies 100, 200, 300 and 400. In use, electrode assembly 500 including cutting electrode 502 and a return electrode 504 (comprised of return electrodes 504a and 504b) is deployed via movable handle 26 of resectoscope 22 from within the sheath 22 (and submerged within the conductive medium, e.g., saline) to an area adjacent a target tissue resection site. Cutting electrode 502 includes a surface finish that includes a combination of a hydrophobic finish 520 coating the cutting electrode 502 and plurality of pits 522. The surface finish of the cutting electrode 502 promotes or facilitates vapor bubble adhesion or minimizes the energy required for bubble nucleation on the cutting electrode 502, which, in turn, minimizes the time delay for an arc to develop at the cutting electrode. Accordingly, an optimum amount of current is shunted through the return electrodes 504a and 504b and current density is concentrated at the cutting electrode 502 such that hemostatic efficacy at the tissue resection site and power transfer from the generator "G" to the cutting electrode 502 is maximized with the electrode assembly 500.

From the foregoing and with reference to the various figure drawings, those skilled in the art will appreciate that certain modifications can also be made to the present disclosure without departing from the scope of the same. For example, in an embodiment, a controller 600 (FIG. 1) may be in operative communication with the generator "G" and/or resectoscope 20 with one or more of the previously described electrode assemblies, e.g., electrode assembly 300, operably coupled to the resectoscope 20. Controller 600 may include one or more modules configured to monitor and/or control one or more electrical parameters (or other suitable parameters) associated with the electrode assembly 300. More particularly, a distance control module 602 may be configured to "virtually" alter the distance between the return electrodes 304a and 304b and the cutting electrode 302 such that specific attributes associated with a desired point along a control curve, e.g., a control curve similar to the curve illustrated in FIG. 4B, may be obtained without actually moving either of the cutting electrode 302 or the longitudinal sections 306 and 308. More particularly, each of the return electrodes 304a and 304b is segmented into one or more return path segments collectively providing a return path for current. More particularly, the distance control module 602 may be configured to selectively open or close each of the return path segments such that the return path for current may be controlled. Thus, in an instance where a distance "d" needs to be increased, the distance control module 602 may open one or more return path segments, e.g., a distal most return segment associated with each of the return electrodes 304a and 304b, such that current is prevented from returning through the distal most return segment associated with each of the return electrodes 304a and 304b effectively increasing the distance of between the return electrodes 304a and 304b and the cutting electrode 302.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrode assembly, comprising:
    a proximal end adapted to connect to an electrosurgical instrument including a housing defining a longitudinal axis therethrough and an electrosurgical energy source;
    a cutting electrode disposed at a distal end of the electrode assembly and having a loop configuration configured to cut tissue;
    first and second return electrodes operably disposed between the cutting electrode and the proximal end of the electrode assembly, the first and second return electrodes separately coupled to respective first and second ends of the loop configuration of the cutting electrode, wherein two bent sections are disposed between the first and second ends of the cutting electrode and the first and second return electrodes, respectively; and
    a dielectric shield extending from a proximal portion of the two bent sections and terminating above and spaced-apart from longitudinal axes of the first and second return electrodes, the dielectric shield extending distally past the cutting electrode to hinder current flow to the first and wherein the dielectric shield includes a first end portion, a middle portion, and a second end portion, the first end portion extending distally and away from the longitudinal axes to the middle portion, the middle portion forming a distally-facing concave configuration, and the second end portion extending from the middle portion distally and towards the longitudinal axes, return electrodes are submersed in a conductive solution and the cutting electrode is energized, thereby concentrating current density at the cutting electrode,
    wherein the dielectric shield forms a concave configuration in a middle portion thereof, and
    wherein the middle portion of the dielectric shield is disposed between the two bent sections and above and spaced-apart from the longitudinal axes of the first and second return electrodes.

2. An electrode assembly according to claim 1, wherein the dielectric shield is formed from material selected from the group consisting of fluoropolymer, polyimide, polyamide, polyaryl sulfone and silicone plastic.

3. An electrode assembly according to claim 1, wherein a thickness of the dielectric shield ranges from about 0.005 inches to 0.100 inches.

4. An electrode assembly according to claim 1, wherein the cutting electrode is a wire made from metal selected from the group consisting of tungsten, tungsten alloys and stainless steel.

5. An electrode assembly according to claim 4, wherein a cross-section diameter of the wire ranges from about 0.25 mm to about 4 mm.

6. An electrode assembly according to claim 1, wherein the loop configuration of the cutting electrode includes a diameter that ranges from about 3 mm to about 10 mm.

7. An electrode assembly according to claim 1, wherein a cross-section of the cutting electrode includes a shape selected from the group consisting of circular, semicircular, square, rectangular, triangular, polygonal and combinations thereof.

8. An electrosurgical instrument, comprising:
    an elongated housing having a lumen defining a longitudinal axis therethrough, the elongated housing having distal and proximal ends, the proximal end adapted to connect to an electrosurgical energy source; and
    an electrode assembly comprising:
        a proximal end adapted to connect to the distal end of the elongated housing;
        a cutting electrode disposed at a distal end of the electrode assembly and having a loop configuration configured to cut tissue;
        first and second return electrodes operably disposed between the cutting electrode and the proximal end of the electrode assembly, first and second return electrodes separately coupled to respective first and second ends of the loop configuration of the cutting electrode, wherein two bent sections are disposed between the first and second ends of the cutting electrode and the first and second return electrodes, respectively; and
        a dielectric shield extending from a proximal portion of the two bent sections and terminating above and spaced-apart from longitudinal axes of the first and second return electrodes, the dielectric shield extending distally past the cutting electrode to hinder current flow to the first and second return electrodes when the dielectric shield, the cutting electrode and the first and second return electrodes are submersed in a conductive solution and the cutting electrode is energized, thereby concentrating current density at the cutting electrode,
        wherein the dielectric shield includes a first end portion, a middle portion, and a second end portion, the first end portion extending distally and away from the longitudinal axes to the middle portion, the middle portion forming a distally-facing concave configuration, and the second end portion extending from the middle portion distally and towards the longitudinal axes, and
        wherein the middle portion of the dielectric shield is disposed between the two bent sections and above and spaced-apart from the longitudinal axes of the first and second return electrodes.

* * * * *